United States Patent
Tanaka et al.

[11] Patent Number: 5,841,004
[45] Date of Patent: Nov. 24, 1998

[54] 3-SUBSTITUTED-α, β-DIBROMOETHYLBENZENE AND PROCESS FOR PREPARING THE SAME

[75] Inventors: Ken Tanaka; Manabu Katsurada; Akemi Hosokawa, all of Kanagawa, Japan

[73] Assignee: Mitsubishi Chemical Corporation, Tokyo, Japan

[21] Appl. No.: 683,772

[22] Filed: Jul. 17, 1996

[30] Foreign Application Priority Data

Jul. 18, 1995 [JP] Japan ................................ 7-181729
Oct. 12, 1995 [JP] Japan ................................ 7-264057

[51] Int. Cl.$^6$ ...................... C07C 17/14; C07C 17/34; C07C 25/04; C07C 25/14
[52] U.S. Cl. ................. 570/127; 570/144; 570/182; 570/197; 570/220; 204/157.65; 204/157.97
[58] Field of Search .................... 570/127, 144, 570/182, 197, 220; 204/157.65, 157.97

[56] References Cited

U.S. PATENT DOCUMENTS 4,954,648  9/1990  Lerman et al. ................. 570/182 X
4,962,246  10/1990  Marhold et al. ................. 570/127

OTHER PUBLICATIONS

Database Darc Eurecas, ACS, RN 79756-83-5, "1-(1,2-dibromoethyl)-3-(trifluoromoethyl)benzene" w/Abstract.
Journal of Chemical Research, Synopses, vol. 1981, No. 9, Sep. 1981, pp. 270-271, XP000653945. Mesnard, D. et al.: "Selection of Methods for the Unequivocal Synthesis of Alkynes. Part 3. Arylacetylenes and 1-Arylalk-1-ynes" * p. 270, col. 1, Line 19 *.
J. Org. Chem. vol. 50, No. 25, pp. 5088-5092, 1985, Marc Halpern, et al., "Hydroxide Ion Initiated Reactions Under Phase Transfer Catalysis Conditions. 9. Dehydrohalogenation of (Haloethyl) Benzenes by Quarternary Ammonium Salts[1]".
J. Org. Chem., vol. 54, No. 13, pp. 3224-3226, 1989, Jihad Dakka, et al., "Bromination of α-Substituted Alkylbenzenes: Synthesis of (p-Bromophenyl)Acetylene".

Primary Examiner—Paul F. Shaver
Attorney, Agent, or Firm—Oblon, Spivak, McClelland, Maier & Neustadt, P.C.

[57] ABSTRACT

A novel 3-substituted α,β-dibromoethylbenzene of formula (I):

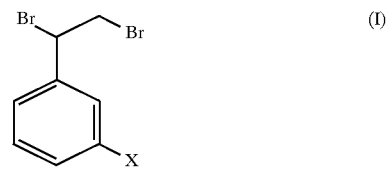

wherein X represents a halogen atom or a trihalomethyl group, which is useful as an intermediate for pharmaceuticals or agricultural chemicals, is prepared by a simple and high yield process which comprises reacting a 3-substituted α-bromoethylbenzene represented by formula (II):

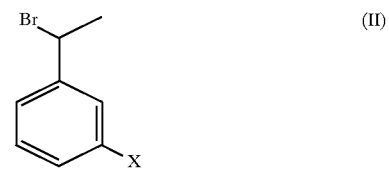

wherein X is as defined above, or a 3-substituted ethylbenzene represented by formula (III):

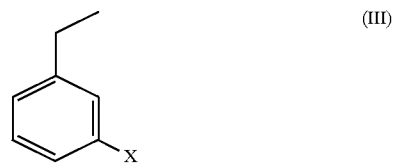

wherein X is as defined above, with bromine in the presence of a quaternary ammonium salt.

16 Claims, No Drawings

3-SUBSTITUTED-α, β-DIBROMOETHYLBENZENE AND PROCESS FOR PREPARING THE SAME

FIELD OF THE INVENTION

This invention relates to a 3-substituted-α,β-dibromoethylbenzen, which is a novel compound useful as an intermediate for pharmaceuticals and agricultural chemicals, and also relates to a process for preparing the 3-substituted-α,β-dibromoethylbenzene.

BACKGROUND OF THE INVENTION

Chlorostyrene oxide derivatives are useful as an antidiabetic agent or an anti-obese agent (see U.S. Pat. No. 5,061,727). Known processes for preparing the 3-chlorostyrene oxide, which is a key intermediate of the chlorostyrene oxide derivatives, include a process of reducing chloro-α-bromoacetophenone followed by cyclization (JP-A-4-218384, JP-A-8-119890, the term "JP-A" as used herein means an "unexamined published Japanese patent application"); a process of epoxidizing chlorostyrene (Yuki Gosei Kagaku, Vol. 43, p. 162 (1987)); and a process starting with chlorobenzaldehyde (JP-A-51-105024).

However, these processes have several disadvantages for industrial application. That is, (1) chloro-α-bromoacetophenone, which is obtained by bromination of chloroacetophenone, is lacrimatory and difficult to handle, (2) industrially available styrenes are limited, (3) reaction reagents used, such as $LiAlH_4$, are expensive, and (4) the yield is low. Therefore, development of a new route for synthesizing 3-chlorostyrene oxide has been demanded.

On the other hand, a substituted-α,β-dibromoethylbenzene is considered useful as a starting material, since this compound can be hydrolyzed to a corresponding bromohydrin compound, which is then cyclized to give a substituted styrene oxide derivative. Nevertheless, only one process is known for preparing α,β-dibromoethylbenzene, in which bromine is added to a styrene compound (Annalen, 154, 154 (1870)). In addition, this process is not practical because industrially available styrene compounds are limited. Therefore, there has been a demand for developing a novel and industrially advantageous process for preparing α,β-dibromoethylbenzene.

SUMMARY OF THE INVENTION

As a result of extensive studies, the inventors have found that a novel 3-substituted-α,β-dibromoethylbenzene which is useful as an intermediate of pharmaceuticals and agricultural chemicals can be obtained by reacting a 3-substituted-α-bromoethylbenzene or a 3-substituted ethylbenzene with bromine in the presence of a quaternary ammonium salt. The present invention was completed based on this finding.

The present invention provides a 3-substituted α,β-dibromoethylbenzene represented by formula (I):

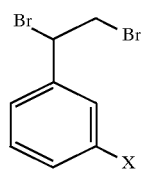

wherein X represents a halogen atom or a trihalomethyl group.

The present invention also provides a process for preparing the 3-substituted a,αβ-dibromoethylbenzene represented by formula (I):

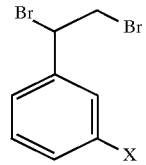

wherein X represents a halogen atom or a trihalomethyl group, which comprises reacting a 3-substituted α-bromoethylbenzene represented by formula (II):

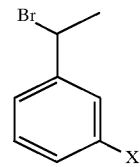

wherein X represents a halogen atom or a trihalomethyl group, or a 3-substituted ethylbenzene represented by formula (III):

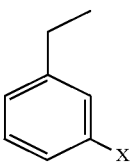

wherein X represents a halogen atom or a trihalomethyl group, with bromine in the presence of a quaternary ammonium salt.

DETAILED DESCRIPTION OF THE INVENTION

Hereinafter, the present invention will be described in detail.

The α,β-dibromoethylbenzene (I) according to the present invention is a novel compound which was synthesized by the inventors for the first time. The substituent X on the benzene ring is a halogen atom or a trihalomethyl group. The halogen atom includes a fluorine atom, a chlorine atom, a bromine atom, and an iodine atom, and the trihalomethyl group includes a trifluoromethyl group, a trichloromethyl group, and a tribromomethyl group. Of the compounds (I), those having a halogen atom (particularly a chlorine atom) as X are useful not only as an intermediate for the above-described pharmaceuticals but also as an intermediate for agricultural chemicals (see JP-A-2-304043). Use of the compounds of the present invention provides new routes for production of the above-described pharmaceuticals and agricultural chemicals which are simpler and more economical than conventional techniques.

For example, in the preparation of the 3-chlorophenylethanolamine derivative described in U.S. Pat. No. 5,061,727, 3-chloro-α,β,-dibromoethylbenzene is converted to a bromohydrin, which is then cyclized to give 3-chlorostyrene oxide, as shown in the following reaction scheme. An optically active styrene oxide can be obtained by optical resolution either before or after the cyclization. Thereafter, the resulting styrene oxide is reacted with a necessary amine compound to obtain a desired compound.

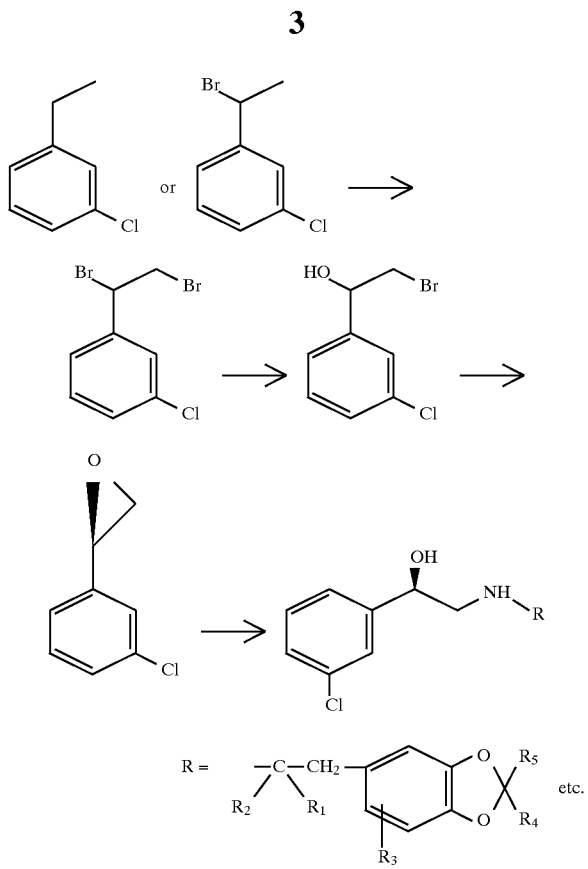

For the preparation of the herbicides having an indanedione skeleton described in JP-A-2-304043, 3-chloro-α,β-dibromoethylbenzene is dehydrobrominated to prepare 3-chloro-α-bromostyrene, as shown in the following reaction scheme. Then, the resulting bromostyrene derivative is converted to an allyl alcohol derivative or an allyl chloride derivative, which is then reacted with an indanedione derivative, followed by epoxidation, to give a desired compound.

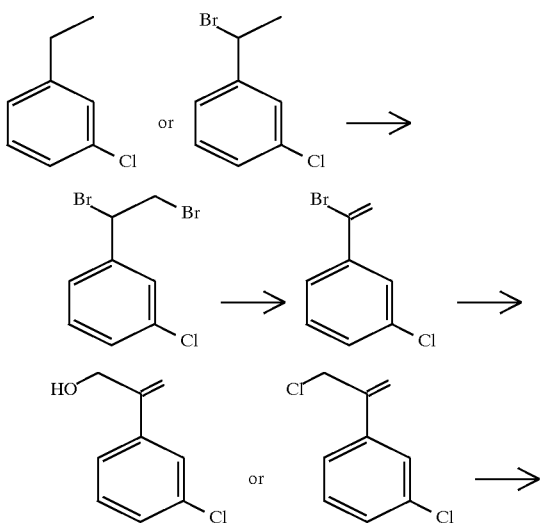

-continued

The α,β-dibromoethylbenzene derivative of formula (I) according to the present invention can be prepared by reacting an a-bromoethylbenzene derivative represented by formula (II) or an ethylbenzene derivative represented by formula (III) with bromine in the presence of a quaternary ammonium base.

The substituent X in the above formulae (II) and (III) is a halogen atom or a trihalomethyl group. The halogen atom includes a fluorine atom, a chlorine atom, a bromine atom, and an iodine atom, and the trihalomethyl group includes a trifluoromethyl group, a trichloromethyl group, and a tribromomethyl group.

The bromination reaction of a substituted benzene nucleus proceeds in the same manner as in bromination of an unsubstituted benzene nucleus irrespective of the position or kind of the substituent on the benzene ring provided that the substituent is an electron attracting group such as a halogen atom, a trihalomethyl group, a nitro group, a cyano group, a sulfo group, an alkyl ester group, etc.

In the reaction to form α,β-dibromoethylbenzene derivative (I) from the a-bromoethylbenzene derivative (II), bromine is used in an amount of 1 to 2 equivalents, preferably 1 to 1.5 equivalents, to the α-bromoethylbenzene derivative (II) in order to assure a satisfactory yield.

In the reaction to form α,β-dibromoethylbenzene derivative (I) from the ethylbenzene derivative (III), bromine is used in an amount of 2 to 3 equivalents, preferably 2 to 2.5 equivalents, to the ethylbenzene derivative (III) in order to assure a satisfactory yield.

When starting with the ethylbenzene derivative (III), a monobrominated compound is once prepared, which is further brominated to the dibrominated compound. The monobromination reaction requires light or a radical initiator. The light irradiation is carried out usually with light having a wavelength of from 200 nm to 800 nm. Commonly employed oil-soluable radical initiators may be used with no particular limitation. Examples of suitable radical initiators include azo compounds such as azobisisobutyronitrile (AIBN) and peroxide compounds such as benzoyl peroxide (BPO). The radical initiator is used in an amount of $0.1 \times 10^{-6}$ to 0.1 equivalent, preferably $0.1 \times 10^{-5}$ to 0.01 equivalent, to the ethylbenzene derivative (III). The reaction is carried out by heating at or above the decomposition point of the radical initiator used.

The bromination reaction is preferably carried out in the absence of a solvent from the standpoint of production efficiency. If desired, the reaction system may be diluted appropriately with an organic solvent. Examples of the suitable solvents include halogenated hydrocarbons such as carbon tetrachloride and chloroform; hydrocarbons such as benzene, cyclohexane, hexane, and heptane; and ethers such as diethyl ether, diisopropyl ether, tetrahydrofuran, and dibutyl ether. While not limiting, the solvent is used in an amount of from 0 to 1000 times, preferably from 0 to 200 times, the volume of the starting compound (i.e., the α-bromoethylbenzene derivative (II) or the ethylbenzene derivative (III)).

The quaternary ammonium salts to be used includes tetramethylammonium hydroxide, tetraethylammonium hydroxide, trimethylbenzylammonium hydroxide, tetramethylammonium bromide, tetraethylammonium bromide, tetrabutylammonium bromide, triethylbenzylammonium bromide, trimethylphenylammonium bromide, triethylbenzylammonium chloride, tetramethylammonium chloride, trioctylmethylammonium chloride, tributylbenzylammonium chloride, trimethylbenzylammonium chloride, N-laurylpyridinium chloride, N-benzylpicolinium chloride, N-lauryl-4-picolinium chloride, N-laurylpicolinium chloride, tricaprylmethylammonium chloride, tetramethylammonium iodide, tetra-n-butylammonium iodide, and tetrabutylammonium hydrogensulfate. Commercially available quaternary ammonium salts may be utilized.

Preferred quaternary ammonium salts are those having a hydrogensulfate ion, a chloride ion or a bromide ion as an anion moiety, such as tetramethylammonium bromide, tetraethylammonium bromide, tetrabutylammonium bromide, triethylbenzylammonium bromide, trimethylphenylammonium bromide, triethylbenzylammonium chloride, tetramethylammonium chloride, trioctylmethylammonium chloride, tributylbenzylammonium chloride, trimethylbenzylammonium chloride, N-laurylpyridinium chloride, N-benzylpicolinium chloride, N-lauryl-4-picolinium chloride, N-laurylpicolinium chloride, and tetrabutylammonium hydrogensulfate. Still preferred are those having a hydrogensulfate ion or a chloride ion as an anion moiety, such as triethylbenzylammonium chloride, tetramethylammonium chloride, trioctylmethylammonium chloride, tributylbenzylammonium chloride, trimethylbenzylammonium chloride, N-laurylpyridinium chloride, N-benzylpicolinium chloride, N-lauryl-4-picolinium chloride, N-laurylpicolinium chloride, and tetrabutylammonium hydrogensulfate.

The amount of the quaternary ammonium salt to be used is important to obtain the compound of the present invention. While it may be different depending on the reaction temperature and the amount of bromine, too much amount of the quaternary ammonium salt is not preferable since bromination on the benzene ring would occur. Generally, the quaternary ammonium salt is used in an amount of $0.5 \times 10^{-3}$ to 0.5 equivalent, preferably 0.001 to 0.1 equivalent, still preferably 0.001 to 0.03 equivalent, to the α-bromoethylbenzene derivative (II) or the ethylbenzene derivative (III).

When the ethylbenzene derivative (III) is used, the quaternary ammonium salt may be added to the reaction system from the very beginning or afterward. From the viewpoint of reaction yield, it is recommended to add the quaternary ammonium salt after 1 equivalent of bromine (to the ethylbenzene derivative) has been added.

The reaction of the α-bromoethylbenzene derivative (II) and bromine is carried out at a temperature of from 20 to 150° C., preferably from 20° to 100° C., more preferably from 50° to 100° C. Bromine is added dropwise, and after completion of the dropwise addition, the reaction is continued for a period of 30 minutes to 3 hours.

The reaction of the ethylbenzene derivative (III) and bromine is carried out at a temperature of from 0° to 200° C., preferably from 20° to 150° C., still preferably from 20° to 100° C. Bromine is added dropwise, and after completion of the dropwise addition, the reaction is continued for a period of 30 minutes to 3 hour.

A preferred mode of the reaction is as follows. One equivalent (based on the ethylbenzene derivative (III)) of bromine in the whole amount of bromine to be used is added dropwise at 0° to 200° C., preferably 0° to 150° C. After the addition of that amount of bromine, the system is allowed to react for a period of 30 minutes to 3 hours. Subsequently, the rest of bromine is added dropwise at 20° to 150° C., preferably 20° to 100° C., more preferably at 50° to 100° C., and after the addition, the system is further allowed to react for a period of 30 minutes to 3 hours, if desired, at an elevated temperature, so as to complete the reaction. The rest of bromine may be added either all at once or in divided portions, and after the addition, the reaction temperature may be raised appropriately during the reaction.

After completion of the reaction, the reaction mixture is cooled to room temperature, washed with an aqueous solution of a reducing agent such as sodium thiosulfate, or an aqueous solution of an alkali such as sodium hydroxide, potassium hydroxide, sodium carbonate or sodium hydrogencarbonate, to remove any unreacted bromine, and extracted with an organic solvent for concentration to isolate the α,β-dibromoethylbenzene derivative (I). If necessary, the product can further be purified by recrystallization, distillation, or the like.

The α-bromoethylbenzene derivative (II) can easily be synthesized by known processes described in the literature, e.g., *J. Org. Chem.*, Vol. 232 (1), pp. 59–70 (1982) and *Collect. Gzech. Chem. Commun.*, Vol. 41 (2), pp. 633–646 (1976). The α-bromoethylbenzene derivative (II) can be easily be synthesized since it is an intermediate formed in the reaction between the ethylbenzene derivative (III) and bromine to prepare the dibrominated compound (I).

The ethylbenzene derivative (III) can easily be synthesized by isomerizing a commercially available monohalo-or trihalomethyl-substituted ethylbenzene to a 3-substituted compound. It can also be prepared by introducing an ethyl group to benzene substituted with a halogen atom, etc. through Friedel-Crafts reaction or by diazotization of commercially available 3-aminoethylbenzene followed by halogenation.

The α,β-dibromoethylbenzene derivative (I) according to the present invention can easily be dehydrobrominated by reacting with a base to give an α-bromostyrene derivative represented by formula (IV):

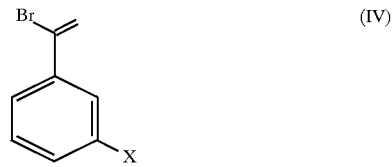

wherein X is a halogen atom or a trihalomethyl group.

Examples of the bases to be used includes inorganic bases such as sodium hydroxide, potassium hydroxide, potassium carbonate, and calcium carbonate; and organic bases such as triethylamine, diazabicycloundecene (DBU), and pyridine.

The amount of the base to be used is not particularly limited provided that it is at least 1 equivalent to the α,β-dibromoethylbenzene derivative (I). The reaction is carried out at −20° to 200° C., preferably 0° to 150° C., still preferably 30° to 120° C., for a period of 10 minutes to 10 hours.

While not limiting, the amount of the solvent is from 0 to 1000 times, preferably 0 to 200 times, the volume of the α,β-dibromoethylbenzene derivative (I).

The dehydrobromination using the base can be carried out in water, an organic solvent, or a two-phase solvent of water and an organic solvent in the presence of a catalyst. It is preferable to add an inorganic base and to carry out the reaction in water or a two-phase solvent of water and an organic solvent in the presence of a catalyst. In this preferred procedure, the treatment after the reaction is easy. Examples of suitable catalysts include quaternary ammonium salts and quaternary phosphonium salts. Since the quaternary ammonium salt that has been used in the preparation of the α,β-dibromoethylbenzene derivative (I) can serve as a catalyst in the dehydrobromination, the reaction may be continued without isolating the α,β-dibromoethylbenzene derivative (I), which is industrially advantageous and preferred.

When water is used as a solvent, the reaction mixture is extracted with an appropriate organic solvent followed by concentration to isolate the α-bromostyrene derivative (IV). When a two-phase solvent of water and an organic solvent is as a solvent, the reaction mixture is subjected to liquid-liquid separation, and the organic layer is collected and concentrated to isolate the α-bromostyrene derivative (IV). If necessary, the product can further be purified by recrystallization, distillation, or the like.

The product as obtained above is distilled under reduced pressure. The degree of vacuum is controlled so that the α-bromostyrene derivative (IV) may be distilled off in a temperature range of from −20° to 200° C., preferably from 0 to 150° C., still preferably from 30° to 120° C.

The present invention will now be illustrated in greater detail with reference to Examples, but it should be understood that the present invention is not construed as being limited thereto. Unless otherwise indicated, all percents, and the like are by weight.

PREPARATION EXAMPLE

Synthesis of 3-Chloro-α-bromoethylbenzene from 3-Chloroethylbenzene

A catalytic amount of AIBN was added to 2.0 g (14.2 mmol) of 3-chloroethylbenzene. Bromine (3.4 g; 21.3 mmol) was added thereto dropwise at 60° C. over a period of 5 minutes under shielding from light, where hydrogen bromide was evolved vigorously. The reaction mixture was stirred at 60° C. for 30 minutes. Gas chromatography analysis of the resulting reaction mixture revealed that 3-chloro-α- bromoethylbenzene had been prepared in a yield of 90% or higher.

Example 1

Synthesis of 3-Chloro-α,β-dibromoethylbenzene from 3-Chloroethylbenzene

To 5.0 g (35.6 mmol) of 3-chloroethylbenzene was added dropwise 6.0 g (37.5 mmol) of bromine at room temperature over a period of 1 hour under irradiation with a 60W fluorescent tube. After the addition, the reaction mixture was further allowed to react at room temperature for 1 hour. Then, 300 mg (1.43 mmol) of tetraethylammonium bromide was dissolved in the reaction mixture, the temperature of the mixture was raised to 80° C., and 6.5 g (40.7 mmol) of bromine was again added over a period of 1 hour. After the addition, the reaction was continued at 80° C. for an additional period of 1 hour to complete the reaction.

The reaction mixture was cooled to room temperature, diluted with diethyl ether, and washed successively with a 10% aqueous solution of sodium hydroxide and a saturated aqueous solution of sodium chloride. The ether layer was dried over anhydrous sodium sulfate and concentrated to give 10.6 g (purity: 90%) of crude crystals of 3-chloro-α, β-dibromoethylbenzene The crude crystals were purified by recrystallization from acetone-water.

Melting point: 39.3–41.4° C.

$^1$H-NMR (δ, CDCl$_3$): 3.96 (1H, t), 4.06 (1H, q), 5.07 (1H, dd), 7.26–7.40 (4H, m)

Example 2

Synthesis of 3-Chloro-α,β-dibromoethylbenzene from 3-Chloroethylbenzene

To 500 g (3.56 mol) of 3-chloroethylbenzene was added dropwise 571 g (3.57 mol) of bromine in the presence of 15 mg (0.0913 mmol) of AIBN at 50° to 60° C. over a period of 1 hour under shielding from light. After the addition, the reaction mixture was stirred for 30 minutes. Then, 6.6 g (0.0355 mol) of benzyltrimethylammonium chloride was added to the reaction mixture, and 571 g (3.57 mol) of bromine was again added dropwise at 60° to 70° C. over a period of 3 hours. After the addition, the temperature was increased to 90° C., and the reaction mixture was further stirred for an additional 1-hour period. Then, 115 g (0.718 mol) of bromine was added dropwise over a period of 1 hour, followed by stirring for 1 hour. After completion of the reaction, the reaction mixture was cooled to room temperature, washed once with a 5% aqueous solution of sodium hydroxide and twice with water to give 1.1 kg (yield: 93%) of 3-chloro-α,β-dibromoethylbenzene as a crude product.

Example 3

Synthesis of 3-Chloro-α,β-dibromoethylbenzene from 3-Chloro-α-bromoethylbenzene

To 10 g (45.6 mmol) of 3-chloro-α-bromoethylbenzene was added 155 mg (0.456 mmol) of tetrabutylammonium hydrogensulfate. The reaction mixture was heated to 40° C., and 8.72 g (54.7 mmol) of bromine was added dropwise at 40° C., followed by stirring at that temperature for 1.5 hours, then at 50° C. for 2 hours, and finally at 70° C. for 2 hours. Gas chromatography analysis of the reaction mixture revealed that 3-chloro-α,β-dibromoethylbenzene had been prepared in a yield of 94%.

APPLICATION EXAMPLE

Synthesis of 3-chloro-α-bromostyrene

In 50 ml of ethanol was suspended 20.8 g (69.7 mmol) of 3-chloro-α,β-dibromoethylbenzene. To the suspension was added 100 ml of an ethanol solution containing 5.8 g (103.4 mmol) of potassium hydroxide at room temperature, and the mixture was stirred at room temperature for 1 hour. After completion of the reaction, the reaction mixture was poured into 150 ml of ice-water and extracted with 300 ml of diethyl ether. The extract was dried over anhydrous sodium sulfate and concentrated to give 15.0 g (purity: 99%) of 3-chloro-α-bromostyrene. $^1$H-NMR (CDCl$_3$, δ): 5.82 (1H, d), 6.14 (1H, d), 7.26–7.33 (2H, m), 7.45–7.49 (1H, m), 7.57–7.58 (1H, m)

As has been fully described above, the present invention makes it possible to prepare novel α,β-dibromoethylbenzene derivatives, which are useful as intermediates for pharmaceuticals and agricultural chemicals, from easily available starting materials in high yield, thereby providing new and simpler and more economical routes to prepare the pharmaceuticals and agricultural chemicals as compared with conventional techniques.

While the invention has been described in detail and with reference to specific examples thereof, it will be apparent to one skilled in the art that various changes and modifications can be made therein without departing from the spirit and scope thereof.

What is claimed is:

1. A 3-substituted α,β-dibromoethylbenzene represented by formula (I):

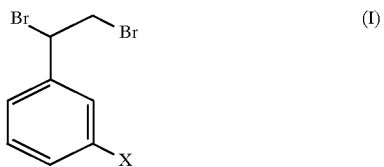

wherein X represents a chlorine, bromine, iodine or trichloromethyl.

2. The compound according to claim 1, wherein X is a chlorine, bromine, or iodine atom.

3. The compound according to claim 1, wherein X is a chlorine atom.

4. A process for preparing a 3-substituted α,β-dibromoethylbenzene of formula (I):

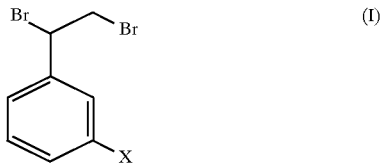

wherein X represents a halogen atom or a trihalomethyl group, which comprises reacting a 3-substituted α-bromoethylbenzene represented by formula (II):

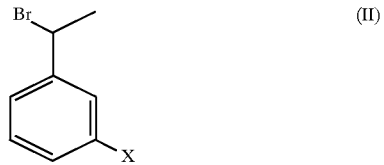

wherein X is as defined above,
or a 3-substituted ethylbenzene represented by formula (III):

wherein X is as defined above,
with bromine in the presence of a quaternary ammonium salt.

5. A process for preparing a 3-substituted α,β-dibromoethylbenzene of formula (I):

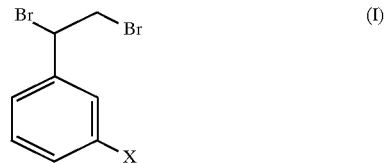

wherein X represents a halogen atom or a trihalomethyl group, which comprises reacting a 3-substituted ethylbenzene represented by formula (III):

wherein X is as defined above,
with bromine in the presence of a quaternary ammonium salt.

6. The process according to claim 4, wherein bromine is used in an amount of from 1 to 2 equivalents to the 3-substituted α-bromoethylbenzene or of form 2 to 3 equivalents to the 3-substituted ethylbenzene.

7. The process according to claim 4, wherein said quaternary ammonium salt has a hydrogensulfate ion, a chloride ion or a bromide ion as an anion moiety.

8. The process according to claim 4, wherein said quaternary ammonium salt is used in an amount of from $0.5 \times 10^{-3}$ to 0.5 equivalent to the 3-substituted α-bromoethylbenzene or the 3-substituted ethylbenzene.

9. The process according to claim 8, wherein said quaternary ammonium salt is used in an amount of from 0.001 to 0.1 equivalent to the 3-substituted α-bromoethylbenzene or the 3-substituted ethylbenzene.

10. The process according to claim 8, wherein said quaternary ammonium salt is used in an amount of from 0.001 to 0.03 equivalent to the 3-substituted α-bromoethylbenzene or the 3-substituted ethylbenzene.

11. The process according to claim 5, wherein said quaternary ammonium salt is added after addition of one equivalent (based on the 3-substituted ethylbenzene) of the whole bromine.

12. The process according to claim 4, wherein said reaction is carried out at a temperature of from 20° to 150° C.

13. The process according to claim 11, wherein said reaction is carried out at a temperature of from 20° to 100° C.

14. The process according to claim 5, wherein the reaction mixture is irradiated with light, or a radical initiator is added to the reaction mixture during the reaction.

15. The process according to claim 11, wherein said radical initiator is added in an amount of from $0.1 \times 10^{-6}$ to 0.1 equivalent to the 3-substituted ethylbenzene.

16. The process according to claim 4, wherein the reaction is carried out in the absence of a solvent.

* * * * *